United States Patent
Koers

(10) Patent No.: US 10,493,402 B2
(45) Date of Patent: Dec. 3, 2019

(54) METHOD AND APPARATUS FOR REMOVAL OF HYDROGEN SULPHIDE FROM GAS MIXTURES WITH MICROORGANISMS

(71) Applicant: Bonno Koers, Doesburg (NL)

(72) Inventor: Bonno Koers, Doesburg (NL)

(*) Notice: Subject to any disclaimer, the term of this patent is extended or adjusted under 35 U.S.C. 154(b) by 0 days.

(21) Appl. No.: 15/738,079

(22) PCT Filed: Jun. 17, 2016

(86) PCT No.: PCT/NL2016/050433
§ 371 (c)(1),
(2) Date: Dec. 19, 2017

(87) PCT Pub. No.: WO2016/204616
PCT Pub. Date: Dec. 22, 2016

(65) Prior Publication Data
US 2018/0304196 A1    Oct. 25, 2018

(30) Foreign Application Priority Data

Jun. 19, 2015 (NL) .................................. 2014997

(51) Int. Cl.
| | | |
|---|---|---|
| B01D 53/84 | (2006.01) | |
| B01D 53/52 | (2006.01) | |
| B01D 53/80 | (2006.01) | |
| B01D 53/96 | (2006.01) | |
| C10G 32/00 | (2006.01) | |

(Continued)

(52) U.S. Cl.
CPC ............ *B01D 53/52* (2013.01); *B01D 53/84* (2013.01); *B01D 53/96* (2013.01); *C01B 17/74* (2013.01); *C02F 3/302* (2013.01); *C02F 3/348* (2013.01); *C10G 32/00* (2013.01); *C12M 47/18* (2013.01); *B01D 53/80* (2013.01); *B01D 2251/102* (2013.01); *B01D 2251/95* (2013.01); *B01D 2256/245* (2013.01); *B01D 2257/30* (2013.01); *B01D 2257/304* (2013.01);
(Continued)

(58) Field of Classification Search
None
See application file for complete search history.

(56) References Cited

U.S. PATENT DOCUMENTS

| | | | |
|---|---|---|---|
| 2008/0311640 A1* | 12/2008 | Cox .......................... | C12P 3/00 435/168 |
| 2014/0329299 A1 | 11/2014 | Guenther ........... | B01D 53/1462 |

FOREIGN PATENT DOCUMENTS

| | | | | |
|---|---|---|---|---|
| DE | 102008031832 | 1/2010 | ............ | C12M 1/107 |
| EP | 0244659 | 4/1987 | ............ | B01D 53/34 |

(Continued)

OTHER PUBLICATIONS

International Preliminary Report on Patentability issued in application No. PCT/NL2016/050433, dated Dec. 19, 2017 (8 pgs).

(Continued)

*Primary Examiner* — Daniel Berns
(74) *Attorney, Agent, or Firm* — Hayes Soloway P.C.

(57) ABSTRACT

Provided is a method for treatment of gas mixtures and an apparatus for carrying out a method for treatment of raw gas mixtures. More particularly, there is provided a method and an apparatus for treatment of gas mixtures, such as biogas or flare gas, and in particular to a method and an apparatus for removing contaminants, in particular $H_2S$, from a gas mixture containing $CH_4$ and $H_2S$.

8 Claims, 2 Drawing Sheets

(51) Int. Cl.
- *C01B 17/74* (2006.01)
- *C12M 1/00* (2006.01)
- *C02F 3/30* (2006.01)
- *C02F 3/34* (2006.01)
- *C02F 101/10* (2006.01)
- *C02F 103/18* (2006.01)
- *C02F 103/20* (2006.01)
- *C02F 103/36* (2006.01)

(52) U.S. Cl.
CPC .... *B01D 2258/05* (2013.01); *C02F 2101/101* (2013.01); *C02F 2103/18* (2013.01); *C02F 2103/20* (2013.01); *C02F 2103/365* (2013.01); *Y02A 50/2358* (2018.01); *Y02P 20/59* (2015.11); *Y02W 10/12* (2015.05)

(56) References Cited

FOREIGN PATENT DOCUMENTS

| | | | |
|---|---|---|---|
| GB | 2262457 | 6/1993 | ............ C01B 17/775 |
| JP | 2002079036 | 3/2002 | ............ B01D 53/14 |
| WO | WO0053290 | 9/2000 | ............ B01D 53/84 |
| WO | WO2012079586 | 6/2012 | ............ B01D 53/52 |
| WO | WO2013087046 | 6/2013 | ............ B01D 53/14 |

OTHER PUBLICATIONS

International Search Report and Written Opinion issued in application No. PCT/NL2016/050433, dated Oct. 4, 2016 (11 pgs).

\* cited by examiner

METHOD AND APPARATUS FOR REMOVAL OF HYDROGEN SULPHIDE FROM GAS MIXTURES WITH MICROORGANISMS

The present invention relates to a method for treatment of gas mixtures and an apparatus for carrying out a method for treatment of raw gas mixtures.

BACKGROUND OF THE INVENTION

This invention relates to a method and an apparatus for treatment of gas mixtures, such as biogas or flare gas, and in particular to a method and an apparatus for removing contaminants, in particular hydrogen sulphide, from a gas mixture comprising hydrogen sulphide, in particular hydrogen sulphide and methane.

Gas mixtures produced and used in industry may contain contaminants.

For instance, biogas is a gas mixture that can be produced by anaerobic digestion with anaerobic bacteria, which break down the organic carbon in the raw materials to a biogas which is mainly comprised of methane ($CH_4$) but which contains contaminants such as carbon dioxide ($CO_2$) nitrogen ($N_2$) and hydrogen sulphide ($H_2S$).

When natural gas is produced as a by-product of industrial processes, for instance in oil industry, operators will often vent or flare the gas mixture produced. This gas is commonly called flare gas. It is common that flare gases are contaminated with $H_2S$. Flare gases commonly also contain methane.

$H_2S$ is very harmful to the environment and human health. It generates an unpleasant smell and even at very low concentrations it can be life threatening. Moreover, it is detrimental to combustion engines. Apart from that, $H_2S$ is in the combustion process converted to sulphur oxides (SOx), which are also harmful to the environment and human health.

Methane can be combusted or oxidized with oxygen to release energy. This energy release allows biogas to be used as a fuel. It can for example be used in gas engines.

There is a continuous need in industry for improved methods and apparatuses which purify methane to acceptable levels of purity and which remove $H_2S$ from gas mixtures.

SUMMARY OF THE INVENTION

The inventor has surprisingly found that $H_2S$ can be efficiently removed from a raw gas mixture by (A) contacting said raw gas mixture with an aqueous slurry comprising anaerobic and aerobic micro-organisms under anaerobic conditions to effect the hydrogen sulphide is at least partially dissolved and converted to other sulphurous compounds in the slurry such that a product stream comprising lower hydrogen sulphide content compared to the raw gas mixture is obtained, (B) subsequently treating the slurry by exposure to aerobic conditions so as to effect aerobic conversion of remaining $H_2S$ or other sulphurous compounds dissolved in the slurry to sulphuric acid, and (C) recycling the major part of the thus obtained sulphuric acid containing slurry as slurry in abovementioned first step.

DESCRIPTION OF THE INVENTION

Figure 1:
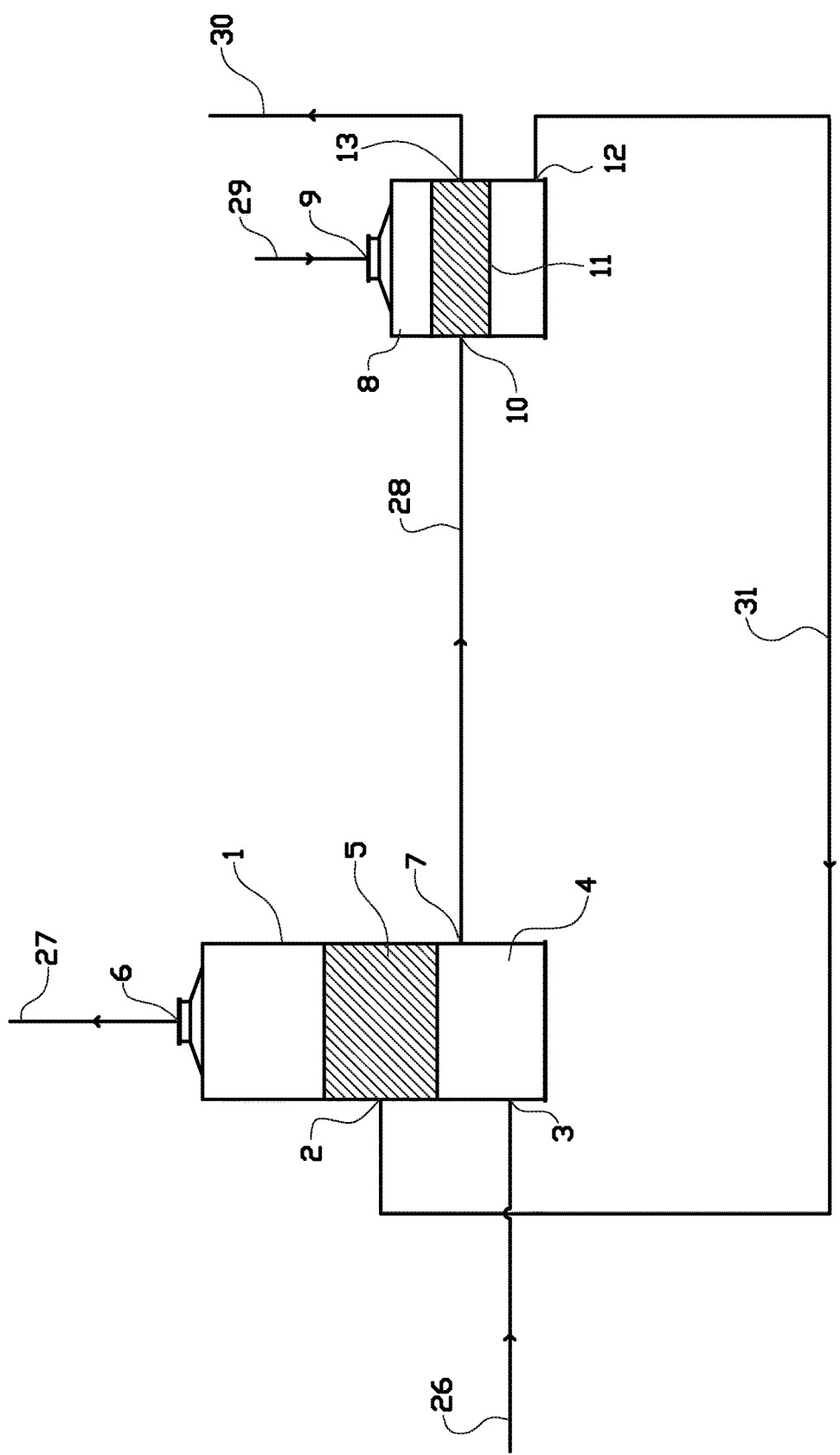
FIG. 1. shows a simplified representation of the apparatus of the invention.

The invention relates in a first aspect to a method for treating a raw gas mixture which contains hydrogen sulphide, comprising introducing a stream of a raw gas mixture containing hydrogen sulphide and a stream of an aqueous slurry comprising anaerobic and aerobic micro-organisms into a first unit, contacting in said first unit said raw gas mixture with said slurry under anaerobic conditions, wherein upon contacting said raw gas mixture with said slurry at least part of the hydrogen sulphide is dissolved and converted to other sulphurous compounds in the slurry such that a product stream comprising lower hydrogen sulphide content compared to the raw gas mixture is obtained, passing said slurry from the first unit to a second unit wherein said slurry is treated by exposure to aerobic conditions so as to effect aerobic conversion of remaining hydrogen sulphide or other sulphurous compounds dissolved in the slurry to sulphuric acid; and recycling a major part of the slurry from the second unit to the first unit.

Because the second unit oxidises the hydrogen sulphide or other sulphurous compounds to sulphuric acid, the slurry which is recycled back to the first unit has a low pH. This has the effect that an acid environment is provided and maintained in the first unit. Due to the anaerobic conditions in the first unit combined with this acid environment, dissolving of $H_2S$ in the first unit is facilitated so that the availability of $H_2S$ for the micro-organisms is increased, which leads to more efficient conversion of $H_2S$.

In addition, the fact that in accordance with the invention conversion of $H_2S$ takes place by applying a first anaerobic step and a second aerobic step the effect is achieved that less sticky sulphur is formed than in $H_2S$ conversion processes which do not apply a first step under anaerobic conditions.

Furthermore, in case the gas mixture also contains $CH_4$ the acidic environment caused by the recycled sulphuric acid containing slurry in combination with the anaerobic environment has the effect that biological loss of $CH_4$ and the risk of explosion due to oxidation of $CH_4$ are reduced to a minimum.

The slurry as applied in the context of the invention is an aqueous slurry comprising anaerobic and aerobic micro-organisms, such as bacteria or mixtures of bacteria which are known in the art for purposes of removing $H_2S$ from gases, liquids or fluids, such bacteria may for example include, amongst others, bacteria belonging to the *Thiobacillus* genus. The slurry may comprise additional food sources for the micro-organisms or other supplements. The method of the invention allows the use of said slurry without the need for harmful chemicals. In this respect it is preferred that no chemicals that are harmful for health and environment are added to the slurry throughout the process.

The inventor has surprisingly found that when the $H_2S$ removal from the gas mixture is performed in accordance with the method of the invention less formation of sticky sulphur takes place compared to prior art methods of removing $H_2S$. Sticky sulphur may lead to clogging of the system used for the $H_2S$ removal method and will limit the life time of an apparatus used for such method.

Moreover it allows a continuous flow of slurry through the units ensuring a stable population of the required anaerobic and aerobic micro-organisms. In this respect the method provides the possibility of a continuous process.

Due to the anaerobic washing of the raw gas mixture to provide a product stream comprising methane and lower hydrogen sulphide content compared to the raw gas mixture in an anaerobic phase in combination with aerobic conversion of remaining $H_2S$ or other *sulphurous* compounds dissolved in the slurry to sulphuric acid the methane is purified in a manner that prevents oxidation of methane and therefore reduces the risk of explosion to a minimum and that results in removal of $H_2S$ in an efficient way to acceptable levels in the range of less than 50 ppmv, even down to about 10 ppmv. The recycling of the major part of the slurry which exits the second unit to the first unit provides an anaerobic and acid environment in the first unit which increases $H_2S$ dissolving and conversion in the slurry. This way the major part, even more preferably substantially all, most preferably all of the $H_2S$ present in the raw gas mixture is dissolved during the anaerobic stage of the method of the invention. The major part (i.e. more than 50%) should be recycled in order to maintain a sufficient biological activity of the slurry.

The raw gas mixture may in particular be a raw gas mixture containing methane and hydrogen sulphide. In this respect the invention relates in a particular preferred embodiment to a method for treating a raw gas mixture which contains methane and hydrogen sulphide, comprising introducing a stream of a raw gas mixture containing methane and hydrogen sulphide and a stream of an aqueous slurry comprising anaerobic and aerobic micro-organisms into a first unit, contacting in said first unit said raw gas mixture with said slurry under anaerobic conditions, wherein upon contacting said raw gas mixture with said slurry at least part of the hydrogen sulphide is dissolved and converted to other sulphurous compounds in the slurry such that a product stream comprising methane and lower hydrogen sulphide content compared to the raw gas mixture is obtained, passing said slurry from the first unit to a second unit wherein said slurry is treated by exposure to aerobic conditions so as to effect aerobic conversion of remaining hydrogen sulphide or other sulphurous compounds dissolved in the slurry to sulphuric acid; and recycling the major part of said slurry from the second unit to the first unit.

In particular when the gas mixture contains methane and $H_2S$ the recycling of the major part of the slurry from the second unit to the first unit provides an acid environment which in combination with the anaerobic conditions in the first unit reduces biological loss of $CH_4$ to a minimum, while increasing $H_2S$ dissolving and conversion in the slurry.

It is preferred that the product stream is further purified by washing the product stream with water, preferably potable water. This is also referred to as polishing.

It is preferred that in the first unit, a first step takes place wherein said raw gas mixture containing hydrogen sulphide is contacted with said slurry by means of a continuous flow of said slurry to effect that hydrogen sulphide is at least partially dissolved and converted to other sulphurous compounds in the slurry such that a product stream comprising lower hydrogen sulphide is obtained and that subsequently a second step in which said product stream is further washed by intermittently spraying the product stream with water takes place.

It is even more preferred that in the first unit, a first step takes place wherein a raw gas mixture containing methane and hydrogen sulphide is contacted with said slurry by means of a continuous flow of said slurry to effect that hydrogen sulphide is at least partially dissolved and converted to other sulphurous compounds in the slurry such that a product stream comprising methane and lower hydrogen sulphide is obtained and that subsequently a second step in which said product stream is further washed by intermittently spraying the product stream with water takes place.

In the first anaerobic step the raw gas mixture is washed first by means of said slurry in a first chamber (washing chamber). While washing the gas mixture with just water to obtain similar $H_2S$ dissolving results will take an enormous amount of water, and with caustic a large amount of caustic, the slurry will absorb/dissolve the $H_2S$ easily. This is due to the biological conversion of the $H_2S$ by the micro-organisms, immediately after the $H_2S$ is dissolved into the slurry. This has the effect that hydrogen sulphide is better dissolved and converted to other sulphurous compounds in the slurry compared to when a non-biological agent (such as water or a caustic composition) would be used. The slurry now contains the dissolved $H_2S$, and the converted products of the biological conversion, i.e.: $HS-$, $S$, $CS_2$, $COS$ and other reduced sulfur compounds. In said second anaerobic step a polishing step will take out the remaining $H_2S$ from the product gas stream to further purify the product stream. This second anaerobic step takes place in a second chamber by intermittently spraying the product stream with water, preferably potable water and results in a cleaned up product stream (preferably comprising methane) and less than 50 ppmv of $H_2S$ and a waste mixture of water and dissolved $H_2S$. This result can be obtained even when the initial raw gas mixture contained amounts as high as for example 5500 ppmv. The slurry from the anaerobic washing chamber can be pumped out of the wash phase into the second, aerobic, unit. The slurry (optionally blended with abovementioned waste mixture from the second anaerobic chamber before entry into the aerobic second unit) is introduced, preferably by spraying, into the second unit and mixed with an oxygen containing gas mixture, preferably ambient air. In this phase the slurry is fully aerated and substantially all or all of the sulfur compounds are converted into sulfuric acid. If the method is performed this way a 3-5 weight % sulfuric acid drain will exit the second unit. This acid drain is recycled into the washing chamber, ready to dissolve the $H_2S$ again.

To maintain the sulfuric acid concentration so that it will not turn into a too concentrated acid and that it will still be capable of dissolving $H_2S$, a small percentage of the flow is refreshed with potable water. It is preferred that the sulphuric acid in the slurry from the second unit is brought to a concentration of between 2 and 4% (by weight), preferably approximately 3% (by weight) before being introduced into the first unit. Depending on the conditions higher percentages of sulphuric acid in the slurry entering the first unit may also be acceptable.

The raw gas mixture may be any gas comprising $H_2S$, i.e. any sour gas. The method of the invention may therefore be applicable to any sour gas.

In one preferred embodiment the raw gas mixture is biogas. The term biogas typically refers to a mixture of different gases which are produced by the digestion of organic matter in the absence of oxygen. Sources for biogas can be raw materials such as agricultural waste, manure, municipal waste, plant material, sewage or petrochemical waste.

In another preferred embodiment the raw gas mixture is flare gas.

In a second aspect the invention relates to an apparatus which is suitable to perform the method of the invention. The features of the apparatus will now be explained by reference to FIG. 1. FIG. 1 is a simplified representation of the apparatus of the invention.

FIG. 1 shows an apparatus for treating a raw gas mixture which contains hydrogen sulphide (in a particular preferred embodiment methane and hydrogen sulphide), comprising a first unit (1), which when in operation is an anaerobic unit. This first unit comprises an inlet (2) for receiving an aqueous slurry comprising anaerobic and aerobic micro-organisms, an inlet (3) for receiving said raw gas mixture; a first chamber (4) in connection with said inlet (2) for receiving said aqueous slurry comprising anaerobic and aerobic micro-organisms and said inlet (3) for receiving said raw gas mixture, said first chamber comprising a structure (5) for facilitating diffusion between said slurry and said raw gas mixture, so as to enable at least partial dissolving hydrogen sulphide and at least partial converting hydrogen sulphide to other sulphurous compounds in the slurry such that a product stream comprising lower hydrogen sulphide content compared to the raw gas mixture (in a particular preferred embodiment a product stream comprising methane and lower hydrogen sulphide content compared to the raw gas mixture) is obtained; an outlet (6) for passing out said product stream, and an outlet (7) for said slurry via which the slurry can be passed to a second unit which is an aerobic unit under operational conditions.

The apparatus of the invention further comprises a second unit (8) comprising an inlet (9) for an oxygen containing gas in order to allow aerobic conditions in the second unit; an inlet (10) in connection with said outlet (7)m for said slurry of the first unit (1) for receiving slurry from said first unit; a structure (11) for facilitating diffusion of said slurry with the oxygen containing gas so as to allow aerobic conversion of any remaining $H_2S$ or other sulphurous compounds dissolved in the slurry to sulphuric acid; an outlet (12) for said slurry; and a gas outlet (13) in connection with the surroundings to allow release of gas. The units, outlets and inlets and other elements of the apparatus are interconnected or connected with the surroundings by connection means (26, 27, 28, 29, 30, 31)

In the apparatus of the invention said outlet (12) for said slurry of the second unit is in connection with the inlet (2) for slurry of the first unit so as to enable recycling of the major part of said slurry from the second unit to the first unit. As mentioned above in respect of the method of the invention, the recycling of the major part of the slurry from the second unit to the first unit provides an anaerobic and acid environment which increases $H_2S$ dissolving and conversion in the slurry. In particular when the gas mixture contains methane and $H_2S$ the recycling of the major part of the slurry from the second unit to the first unit provides an anaerobic and acid environment which reduces biological loss of $CH_4$ to a minimum, while increasing $H_2S$ dissolving and conversion in the slurry.

The skilled person will understand that connections between the units, inlets, outlets can be provided by any connections means that enable a stream of gases, fluids or liquid such as tubings or pipes. Likewise the inlets and outlets of the apparatus can be provided with any suitable tubing or pipe that enables entry or exit of gases, fluids or liquids from chambers and/or units.

The apparatus preferably further comprises in the first unit a second chamber which is in connection with the first chamber, comprising a structure for facilitating diffusion of water and said product stream and a means for providing an intermittent flow of water into the second chamber so as to enable removing any residual hydrogen sulphide from the product stream from said first chamber. The incorporation of this element provides the opportunity of applying a step to "polish" the product stream, which in a preferred embodiment contains methane, from the first chamber to obtain a further cleaned up product stream comprising less than 50 ppmv of $H_2S$.

The first and the second chamber are preferably separated by a water collector. The water collector may have a connection to a buffer tank in order to pass a waste mixture of water and dissolved $H_2S$ into a buffer tank in which it can be mixed with the slurry from the first chamber. Over time, it might be that the polishing step builds-up elementary sulfur. The collector allows washing said structure for facilitating diffusion. Washing the structure elementary sulphur may suitably be effected by rinsing the structure with a caustic mixture.

Downstream of the first and second chamber of the first unit (the anaerobic unit) a buffer tank may be provided in which the anaerobic wash slurry which contains the dissolved $H_2S$, and the converted products of the biological conversion, i.e.: HS—, S, $CS_2$, COS and other reduced sulfur compounds from the first chamber and the mixture of water and dissolved residual $H_2S$, and the converted products of the biological conversion, i.e.: HS—, S, $CS_2$ from the second chamber is collected and optionally buffered to adjust the pH. The buffer tank may be provided with an inlet for water and an outlet for removing liquid to a sump. This allows to optimize the composition introduced into the second unit (the aerobic unit), for the biological breakdown of the sulphurous compounds contained therein to sulphuric acid. In a preferred embodiment the apparatus further comprises a means for lowering the sulphuric acid concentration in the slurry positioned between the outlet for said slurry of the second unit and the inlet for said slurry of the first unit. This allows to maintain the sulfuric acid concentration so that it will not turn into a too concentrated acid and that it will still be capable of efficiently dissolving $H_2S$ when the slurry is recycled into the first unit.

The apparatus may suitably be provided with a blower to bring the right amount of ambient air into the second unit to allow for the full oxidation process of the anaerobic slurry from the first unit. Vents may also be added in the apparatus where gases need to be ventilated out of the apparatus.

The apparatus may be suitably provided with pumps to pump the gases, fluids or liquids to and from the respective compartments.

The structures in the first unit and second unit which serve to optimize diffusion of the gases, fluids and/or liquids are preferably synthetic structures. Structures that may be suitable for these purposes are known in the art and may be filter packages made of plastics such as HDPE or polypropylene. An example of a suitable filter package is described in US2010/0089818. Such structures are commonly referred to in the art as structured packing. The micro-organisms used in slurry perform their activity in the slurry, but can also sediment from the slurry onto the structures in biofilms, where they can also perform their activity of degrading $H_2S$ in accordance with the method of the invention to sulphuric acid.

Exemplary Embodiment

In the following paragraph an exemplary embodiment of the apparatus of the invention will be explained with reference to FIG. 2.

Figure 2:
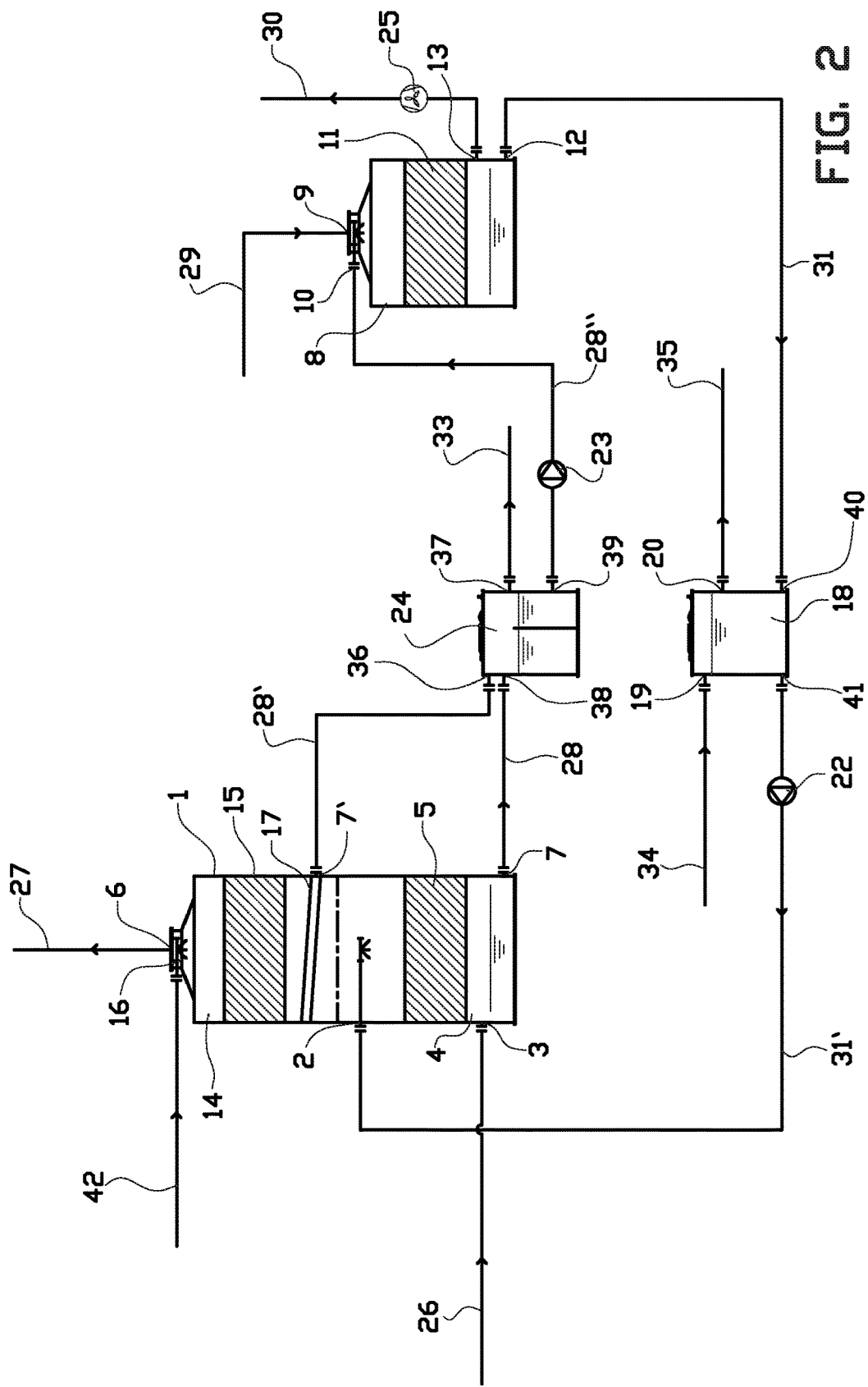
FIG. 2. shows an exemplary embodiment of the apparatus of the invention.

FIG. 2 shows an exemplary embodiment of the apparatus of the invention in which a raw gas mixture comprising methane and hydrogen sulphide is passed via piping (26) and inlet (3) into the first chamber (4) of a first unit (1). The first unit (3) also comprises an inlet (2) for receiving via piping (31, 31') an aqueous slurry comprising anaerobic and aerobic micro-organisms. This slurry is introduced into the first chamber (4) in a strong and continuous flow. In the first chamber (4) synthetic and structured media (5) are installed which optimize diffusion between the raw gas mixture and the aqueous slurry and which allow for optimal exchange of components. In this treatment at least part, but preferably most or even more preferably substantially all of the $H_2S$ is absorbed or dissolved into the slurry and at least partially converted to other sulphurous compounds in the slurry. After this treatment the cleaned up gas is passed to a second chamber (14) which is situated above the first chamber. The slurry is passed out of the first chamber (4) via outlet (7) and piping (28). In the second chamber (14) the gas will be "polished" to take out remaining $H_2S$. The second chamber (14) also comprises a structure (15) for facilitating diffusion of the water and gas. In the second chamber any residual hydrogen sulphide is removed from product stream by intermittently spraying the product stream with water by means (16) via piping (42) for providing an intermittent flow of water. The purified methane gas is released from the first unit via outlet (6) and piping (27). The first and the second chamber (4, 14) are separated by a water collector (17) which allows washing said structure for facilitating diffusion, for instance by rinsing the structure with a caustic mixture. The water collector is configured such that flow of the methane containing gaseous product stream from the first to the second chamber is possible, for instance in the form of drain gutters. The first chamber (4) is connected via outlet (7) and piping 28 with inlet (36) of buffer tank (24). The second chamber (14) is connected (optionally via water collector (17)) via outlet (7') and piping (28') with inlet (36) of the buffer tank (24). In the buffer tank the anaerobic wash slurry which contains the dissolved $H_2S$, and the converted products of the biological conversion, i.e.: HS—, S, $CS_2$, COS and other reduced sulfur compounds from the first chamber and the mixture of water and dissolved $H_2S$, and the converted products of the biological conversion, i.e.: HS—, S, $CS_2$ from the second chambers is collected and optionally buffered to adjust the pH. The buffer tank can be connected via outlet (37) and piping (33) to a drain sump to allow draining of excess slurry. From the buffer tank (24) the slurry is passed via outlet (39) and piping (28") to a second unit (8). This unit is provided with an inlet (9) for supplying an oxygen containing gas via piping (29); an inlet (10) in connection via piping (28, 28', 28''') with said outlet of the first unit for receiving slurry from said first unit; a structure (11), preferably a synthetic structure, for facilitating diffusion of said slurry so as to allow aerobic conversion of any remaining $H_2S$ or other sulphurous compounds dissolved in the slurry to sulphuric acid; an outlet (12) for said slurry; and a gas outlet (13) in connection with the surroundings via a pipe (30). In this pipe (30) a vent (25) may be connected to allow ventilation of gases. The outlet (14) for said slurry of the second unit is in connection with the inlet (2) for slurry of the first unit via piping (31, 31') so as to enable recycling of said slurry from the second unit (8) to the first unit (1). The apparatus of this embodiment further comprises a means (18) for lowering the sulphuric acid concentration in the slurry positioned via inlet (40) and outlet (41) in piping (31, 31') between the outlet (12) for said slurry of the second unit (8) and the inlet (2) for said slurry of the first unit (1). Means (18) may be connected to water supply via inlet (19) and piping (34) and a drain sump via outlet (20) and piping (35) in order to enable control of the sulphuric acid content in the slurry before it is recycled back the first unit (1). The apparatus is provided with pumps (22) and (23) to pump the gases, fluids or liquids to and from the respective compartments. The apparatus may also be provided with a blower to bring the right amount of oxygen containing gas (preferably ambient air) into the second unit (8) to allow for the full oxidation process of the anaerobic slurry from the first unit (1). It will be obvious that many changes can be made to the exemplary embodiment according to the invention in the paragraph above without being beyond the inventive idea as it is defined in the claims.

The person skilled in the art will acknowledge that the method and apparatus of the invention can be applied and configured using different dimensions and sizes. For instance biogas may be supplied to the first unit in a flow rate of 765 $m^3/h$. Depending on the wishes of the user this may be lower or higher. For instance sour gas or flare gas may be supplied in flow rates which are about 100 times higher.

The invention claimed is:

1. A method for treating a raw gas mixture which contains hydrogen sulphide, comprising the steps of:
    introducing a stream of a raw gas mixture containing hydrogen sulphide and a stream of an aqueous slurry comprising anaerobic and aerobic micro-organisms into a first unit,
    contacting in said first unit said raw gas mixture with said slurry under anaerobic and acidic conditions, wherein upon contacting said raw gas mixture with said slurry at least part of the hydrogen sulphide is dissolved and converted to elemental sulfur and other sulphurous- and sulfur ion-containing compounds in the slurry such that a product stream comprising lower hydrogen sulphide content compared to the raw gas mixture is obtained,
    passing said slurry from the first unit to a second unit wherein said slurry is treated by exposure to aerobic conditions so as to effect aerobic conversion of remaining $H_2S$, the elemental sulfur and other sulphurous- and sulfur-ion containing compounds dissolved in the slurry to sulphuric acid; and
    recycling the major part of said slurry including dissolved sulfuric acid from the second unit to the first unit.

2. The method according to claim 1, wherein said raw gas mixture contains methane and hydrogen sulphide and the product stream contains methane and lower hydrogen sulphide content compared to the raw gas mixture.

3. The method according to claim 1, comprising the steps of further purification of said product stream by washing the product stream with water.

4. The method according to claim 1, comprising, in the first unit, a first step wherein said raw gas mixture is contacted with said slurry by a continuous flow of slurry to effect that hydrogen sulphide is at least partially dissolved and converted to elemental sulfur and other sulphurous- and sulfur-ion containing compounds in the slurry such that a product stream comprising lower hydrogen sulphide content is obtained and a second step in which said product stream is further washed by intermittently spraying the product stream with water.

5. The method according to claim 1, wherein the sulphuric acid in the slurry from the second unit is brought to a concentration of between 2 and 4 weight % before being introduced into the first unit.

6. The method according to claim 1, wherein the raw gas mixture is a biogas.

7. The method according to claim 1, wherein the raw gas mixture is a flare gas.

8. The method according to claim 1, wherein the other sulphurous- and sulfur ion-containing compounds are selected from the group consisting of HS—, $CS_2$ and COS.

* * * * *